United States Patent [19]

Hillebrand et al.

[11] Patent Number: 6,037,465
[45] Date of Patent: Mar. 14, 2000

[54] UNIVERSAL PROCESS FOR ISOLATING AND PURIFYING NUCLEIC ACIDS FROM EXTREMELY SMALL AMOUNTS OF HIGHLY CONTAMINATED VARIOUS STARTING MATERIALS

[75] Inventors: Timo Hillebrand; Peter Bendzko; Lars-Erik Peters, all of Berlin, Germany

[73] Assignee: Invitek GmbH, Germany

[21] Appl. No.: 08/780,091

[22] Filed: Dec. 16, 1996

Related U.S. Application Data

[63] Continuation of application No. PCT/DE95/00787, Jun. 14, 1995.

[30] Foreign Application Priority Data

Jun. 14, 1994 [DE] Germany ............... 44 22 040
Jun. 14, 1994 [DE] Germany ............... 44 22 044
Dec. 30, 1994 [DE] Germany ............... 44 47 015

[51] Int. Cl.$^7$ ............... C07H 1/06; C12N 15/10
[52] U.S. Cl. ............... 536/25.42; 536/25.4; 435/41.1
[58] Field of Search ............... 435/91.1; 536/25.42, 536/25.4

[56] References Cited

U.S. PATENT DOCUMENTS 5,234,809 8/1993 Boom et al. ............... 435/91.1

*Primary Examiner*—Gary L. Kunz
*Attorney, Agent, or Firm*—Londa and Traub LLP

[57] ABSTRACT

A universal process is disclosed for extracting and purifying nucleic acids from extremely small amounts of highly contaminated various biological and other starting materials. The invention has applications in forensic medicine, medical diagnosis, molecular biology, biochemistry, genetic technology and all related fields. The process is characterized in that nucleic acid-containing materials are lysed, the lysate is incubated with a non-porous, non-structured, highly disperse, homogeneous and chemically pure $SiO_2$ substrate, the substrate is isolated with the bound nucleic acids and washed with a buffer solution, then the nucleic acids are dissolved from the substrate by a buffer with a lower salt concentration. Lysis of the material and nucleic acid immobilization are preferably carried out in a reaction vessel. The substrate particles have a size of 7–40 nm, preferably 40 nm, and a specific surface from 50–300 $g/m^2$, preferably 50 $g/m^2$.

13 Claims, No Drawings

UNIVERSAL PROCESS FOR ISOLATING AND PURIFYING NUCLEIC ACIDS FROM EXTREMELY SMALL AMOUNTS OF HIGHLY CONTAMINATED VARIOUS STARTING MATERIALS

This application is a continuation of PCT/DE95/00787 filed Jun. 14, 1995.

The invention relates to a process for isolating and purifying nucleic acids from extremely small [amounts] of various biological and other starting materials which, under some circumstances, are also highly contaminated with organic as well as inorganic components. The method is of great importance for a plurality of biological, molecular biological, forensic, medical, analytical and biochemical laboratories. With that, the areas of application of the invention are forensic medicine, medical diagnosis, molecular biology, biochemistry, genetic engineering and all other adjoining fields.

Usually, nucleic acids are obtained from cells and tissues by breaking down the starting materials under strongly denaturing and reducing conditions, partially also with use of protein-decomposing enzymes, purifying the emerging nucleic acid fractions by means of phenol-chloroform extraction steps and obtaining the nucleic acids by means of dialysis or ethanol precipitation from the aqueous phase (Sambrook, J., Fritsch, E. F. and Maniatis, T., 1989, CSH, "Molecular Cloning").

These "classical methods" of isolating nucleic acids from cells and particularly from tissues are very time consuming (take longer than 48 hours in some cases), require a considerable expenditure for equipment and, moreover, can also not be realized under field conditions. Furthermore, because of the chemicals used, such as phenol and chloroform, such methods are an appreciable hazard to health.

Various alternative methods for isolating nucleic acids from different biological starting materials make it possible to circumvent the hazardous phenol-chloroform extraction of nucleic acid, as well as to achieve a reduction in the time spent.

All of these methods are based on a method for the preparative and analytical purification of DNA fragments from agarose gels, developed and described for the first time by Vogelstein and Gillespie (Proc. Natl. Acad. Sci. USA, 1979, 76, 615–619). The method combines the dissolving of the agarose, containing the DNA bands to be isolated, in a saturated sodium iodide solution with bonding of the DNA to glass particles in the presence of this chaotropic salt. The DNA, fixed to the glass particles, is subsequently washed with a solution of 20 mM of tris hydrochloride (pH of 7.2), 200 mM of sodium chloride, 2 mM of EDTA in 50% v/v of ethanol and finally dissolved from the carrier particles.

This method has since experienced a series of modifications and is used at the present time for different methods of extracting and purifying nucleic acids from different origins (Marko, M. A., Chippeifield, R. and Bimboim, H. G., 1982, Anal. Biochem., 121, 382–387).

Moreover, there is at the present time a plurality of reagent systems worldwide, particularly for the purification of DNA fragments from agarose gels and for the isolation of plasmid DNA from bacterial lysates, but also for the isolation of longer-chain nucleic acids (genomic DNA, cellular total RNA) fiom blood, tissue or also cell cultures.

For example, the EP-A-389 063 discloses a method for isolating nucleic acids, according to which carrier materials with a particle size between 50 and 500,000 nm are used.

All of these commercially available kits are based on the well known principle of bonding nucleic acids to mineral carriers in the presence of highly molar solutions of different chaotropic salts and using finely ground glass powder (such as glass milk, BIO 101, La Jolla, Calif.) diatomaceous earths (Sigma) or also silica gel (Diagen, DE 41 39 664 A1) as carrier materials.

However, neither classical glass milk or diatomaceous earth suspensions nor silica gels fixed on chromatographic columns fulfill the physical prerequisites required for the isolation of very small amounts of nucleic acids. Furthermore, such physical characteristics as porous or structured surfaces, as well as surfaces of these carrier materials of relatively low activity have an unfavorable effect on the removal of contaminants.

For example, it is not possible to isolate DNA, which can be used for PCR, from saliva samples using glass milk (Ochert, A. S. et al.; 1993, PCR Methods and Application, 3, 6, 365–368). The DNA, bound to the glass particles, cannot be washed adequately and probably also itself bonds, for example, low molecular weight sugar compounds, so that these contaminants, which are contained in the saliva, are also to be found in the final DNA and inhibit subsequent enzymatic reactions (such as PCR).

According to the state of the art, there is also no efficient and rapid method, which permits genomic (or also bacterial or viral) DNA to be isolated from stool samples. Stool material from biological starting material is extremely highly contaminated and makes very high demands on a DNA isolating system.

Methods employed at the present time for the isolation of DNA from stool samples in some cases require several days and include expensive proteinase K digestions and phenol/chloroform extractions as well as ethanol precipitations and furthermore require yet another purification of the already isolated nucleic acids using the known DNA bonding to glass particles.

A further problem of the glass materials or columns containing porous silica gels, used at the present time for the isolation of genomic (and, with that, longer chain) DNA lies in the very high mechanical stresses (shearing) exerted on the high molecular weight DNA.

Genomic DNA, isolated with glass milk or diatomaceous earth suspensions, as well as with mini columns containing silica gel, frequently shows clearly visible degradations by gel electrophoresis (especially when mini column systems are used). The cause for this lies, on the one hand, in the mechanical stresses, to which the DNA is subjected during passage through the pores of the silica gels or through the carrier suspensions containing glass powders or diatomaceous earths, which do not have a homogenous particle consistency (diatomaceous earth, for example, also contains particles with very sharp edges and, moreover, does not have a homogenous size). Accordingly, every washing or centrifugation step leads to a degradation of the DNA.

The binding of cellular total RNA to, for example, silica gel-carrying columns is known and available as a reagent system, but does not realize complete isolation of cellular total RNA, since smaller RNA species (<200 bp) can no longer be isolated. Accordingly, such an RNA, for example, can no longer be used successfully for DDRT-PCR applications (isolation of all mRNA species of a cell) since, from the outset, small RNA species are not present. Moreover, the isolation of RNA from extremely small amounts of starting materials is not possible with such systems. Although methods of isolating as well as of purifying nucleic acids by means of the well known principle of binding the nucleic acids to mineral materials is meanwhile widespread, a series of [problems involving] special uses of the isolation of nucleic acids are not or not satisfactorily solved with the previously known methods of isolation (and the carrier materials used).

This relates to:

1. the isolation of nucleic acids (genomic DNA, total RNA) fiom extremely small amounts of starting materials (such as <0.5 mg of tissue material, 0.5 µL of blood or blood traces on clothing, <5 µL of saliva or <10³ cells,
2. the availability of a universal system for the isolation of nucleic acids from a very broad spectrum of different starting materials (that is, the isolation of nucleic acids from "simple starting materials" such as cell cultures or whole blood, as well as from extremely difficult starting materials, such as very old bones or stool materials),
3. the isolation of nucleic acids from highly contaminated starting materials in a quality, which permits the isolated nucleic acids to be used successfully also as a substrate for enzymatic secondary reactions (such as PCR).

Especially such contaminated starting materials are of great importance for certain clinically relevant problems in diagnosis, for forensic analyses or the clarification of questions of biological evolution. Such "interesting" starting materials include, above all, bones or traces of blood on clothing (forensic medicine), very old bones (biological evolution), saliva, bronchial sputum and stool samples (medical diagnosis). As already stated, it is not possible, for example, to isolate DNA, which can be amplified, from saliva samples using glass milk.

This problem is even more complicated when DNA is to be isolated from stool samples. According to the present state of the art, it must be noted clearly that there is not yet a functioning, rapid method of isolation (either commercially available or published) for isolating nucleic acids capable of amplification. Up to now, extremely time-consuming and work-intensive multiple purification steps are required for isolating DNA from such a starting material. Such expensive procedures are necessary, since the majority of contaminations, contained in stool samples, cannot be removed differently with any of the methods known previously. A direct and, with that, very rapid isolation of amplifiable nucleic acids from stool samples by way of bonding the nucleic acids to carrier materials has hitherto not been known. This is a very great disadvantage, since stool material is not available as a source of nucleic acids to be isolated (particularly of genomic DNA from epithelial cells sloughed off from the intestinal wall) for routine gene diagnosis.

It is an object of the invention to provide a universal method for isolating and purifying nucleic acids, which permits these special applications.

Surprisingly, it was found that all of these requirements are fulfilled in an outstanding manner with the carrier material, used pursuant to the invention, and employing different chaotropic salts.

The inventive method is realized in accordance with claims 1 to 12. It is characterized owing to the fact that the starting materials, containing the nucleic acids, are lysed, the lysate is incubated with a nonporous and unstructured, highly disperse as well as homogeneous, chemically pure silica carrier, the carrier, together with the bound nucleic acids, is separated and washed with buffer solution and the nucleic acids subsequently are dissolved from the carrier with a buffer of low salt concentration.

The lysis of materials containing nucleic acids is conducted with buffers, which contain chaotropic salts of high ionic strength.

The nucleic acids are fixed to the surface of silica particles, which have a particle size of 7 to 40 nm and an active surface area of 50 to 300 $m^2/g$ and preferably a particle diameter of 40 nm and an active surface area of about 50 $m^2/g$, in the presence of chaotropic salts of high ionic strength.

As chaotropic salts, preferably guanidine hydrochloride, guanidine thiocyanate, lithium chloride, sodium iodide, potassium iodide, sodium perchlorate or lithium chloride/urea mixtures of an ionic strength in excess of 4M are used.

With that, it becomes possible to isolate nucleic acids from a) extremely small amounts of starting materials containing nucleic acids b) from various very "difficult" biological and other starting materials, such as stool samples, bones, etc., which are highly contaminated with organic and inorganic impurities in a quality and quantity, which make subsequent enzymatic manipulations with the isolated nucleic acids possible.

Equally surprisingly, it was observed that bonding of either DNA or RNA is realized selectively, depending on the chaotropic buffer selected in combination with the carrier material used. With that, solely by selecting the chaotropic salt used for the lysis of the starting material, the carrier material can be used for the isolation of DNA or for the isolation of RNA, no changes having to be made in the method. Such a behavior of a material, used for bonding nucleic acids, has not been described previously.

The method for isolating nucleic acids is handled very easily, requires little in the way of equipment and no enzymatic pretreatment of the sample material (such as a proteinase K digestion), does without the use of a toxic phenolchloroform extraction, does not need an ethanol precipitation and can be realized with little expenditure of time, which permits samples to be processed on a large scale.

The physical properties of the carrier material, used pursuant to the invention, are ideal for isolating and purifying nucleic acids from extremely small amounts of various starting materials, as well as fiom starting materials highly contaminated with impurities. The properties of the selected carrier material, on which the invention is based and which are compared in the following with those of other carrier materials, for the first time enable a universal system to be developed for the isolation of nucleic acids (universal in the sense that DNA as well as RNA and nucleic acids can be isolated from all biological and other starting materials containing nucleic acids, as well as in the sense that nucleic acids can be isolated from extremely small amounts of starting materials as well as from starting materials highly contaminated with impurities). As furthermore indicated, such a universal system cannot be realized with conventionally used glass materials (glass milk, glass powder, etc.).

The carrier material, used in the invention, differs with respect to its physical characteristics basically from other carrier materials, which are used for the isolation of nucleic acids and which usually [are] not chemically pure silica, but are porous or nonporous glass materials, such as those based on borosilicate glass (glass milk) or mineral cell wall components from plants (diatomaceous earths), which are available commercially as chromatographic materials for applications in the purification of nucleic acids and, with that, form the basis for producing (also the commercially available) suspensions. All of these carrier materials are very well suited for standard applications; however, because of their physical structure, they exhibit appreciable disadvantages or limitations for the isolation of nucleic acids from the starting materials described above.

The carrier material, used in the inventive method, is significantly smaller than previously used materials.

Consequently, the active carrier surface area, available for fixing the nucleic acids, is very much larger. Particularly the size of the carrier particles, which is defined only in the nm range, as well as the therefrom resulting very high specific surface area, enable nucleic acids to be isolated from extremely small amounts of starting material. Moreover, the objective of isolating nucleic acids from extremely small amounts of various starting materials, which forms the basis of the inventive method, in the final analysis also corresponds to a new strategy, which is to make it possible to prepare a compound by already existing methods as well as by methods of so-called non-invasive medical sampling (micro amounts of microbiopsy materials still being developed; obtaining epithelial lung cells with specially constructed "expired air collectors", etc.) and by methods of medical diagnosis. It has previously not been possible to isolate for further diagnosis nucleic acids from extremely small samples containing the nucleic acids (such as biopsy materials, lung fluids). With that, the isolation of nucleic acids from such extremely small amounts of starting materials, realized with the inventive method, opens up new potential areas of application for the first time to the new non-invasive methods in medical sampling.

A further important advantage of the carrier particles, used in the inventive method, consists in the direct binding and with that in the direct exposure of the nucleic acids on the carrier surface. In contrast to this, in the case of the chromatographic systems used (for example, in the DE 41 39 664 A1), which employs a combination of porous anionic exchange resins and mineral carriers, the nucleic acids, which are to be isolated, are not on the surface and instead are within the pores.

Such a localization greatly reduces the possibility of washing intensively and, with that, of removing the different contaminants. Likewise, because of the much larger particle size (as well as because some of the carrier particles are not homogeneous mixtures) and the therewith associated smaller surface area of the carrier, glass milk suspensions, suspensions of diatomaceous earth or porous or nonporous matrixes described in the German patent DE 41 39 664 A1 (ranging in size from 1 $\mu$m to 250 $\mu$m and preferably from 10 $\mu$m to 30 $\mu$m) do not make it possible to wash the bound nucleic effectively. The absence of such an intensive washing becomes a problem especially when nucleic acids are to be isolated from starting materials, which contain enormous amounts of very different contaminations, such as mucins, dyes, low molecular weight sugar compounds, etc.

The inventive method with the carrier material used for the first time offers the possibility of isolating DNA directly from cells, which have flaked off from intestinal walls, without expensive proteinase K digestions, phenol/chloroform extractions and ethanol precipitations. After the insoluble components have been removed from the stool sample and a buffer, containing a chaotropic salt has been added, the DNA is bound directly to the carrier material, washed and eluted from the carrier. This method is extremely fast (about 1 hour) and supplies genomic DNA of excellent quality, which can be used without problems for PCR applications. Such a fast method of isolating amplifiable DNA from stool material has not been attained previously with any other DNA isolating system. This makes it possible for the first time, for example, to carry out a rapid and reproducible detection of point mutations in the proto-oncogen, which is associated with colon cancer, as a genetic diagnostic method, which will be important in the future and, with that, becomes important for protective measures for risk groups or in the early detection of colon carcinomas or also of pancreatic carcinomas. Such a routine genetic diagnosis was previously impossible because of the absence of a suitable method of isolating and purifying genomic DNA.

The carrier material, used in the inventive method and selected from such points of view, also greatly reduces (in contrast to other carrier materials or column systems) mechanical stresses on the DNA because of the fineness of the particles and because of the homogeneity and also owing to the fact that it is not a question of crushed glass materials or diatomaceous earths. Accordingly, and this is also shown very clearly by a gel electrophoretic representation, the isolated DNA has a high degree of integrity and, with that, is of a quality comparable to that of DNA obtained by the very gentle, classical phenol/chloroform extraction method. Genomic DNA of high integrity is required especially when the DNA is to be used as a substrate for LA/XL-PCR applications or DNA fingerprint techniques.

A further advantage of the inventive method consists therein that the carrier material used is also suitable ideally for the isolation of ribonucleic acids (RNA) and, in contrast to the mini-columns (available from Diagen), which are charged with silica matrixes and used at the present time for the isolation of RNA, also makes it possible to isolate cellular total RNA, that is, to isolate also very small RNA species.

The inventive method permits the isolation of cellular total RNA, including tRNA and 5A RNA fractions (and, with that, also all small RNA species), as well as the isolation of RNA from a few hundred cells and, with that, from extremely small starting amounts. It is therefore outstandingly suitable for expression investigations of very small amounts of cells, particularly since the whole procedure of isolating the total RNA from such starting materials takes only about 20 minutes.

Furthermore, the very large specific surface area of the carrier particles provides a very high binding efficiency, so that theoretically 100% of the RNA, present in the various starting materials, can also be isolated. This is particularly important when quantitative PCR applications are to be developed, for example, in hepatitis C diagnosis, in order to obtain information concerning the course of the virus titer in the blood. The use of a quantitative PCR for answering such questions accordingly depends to a large extent on the system used to isolate the RNA.

The bonding of the RNA molecules to the carrier material used is accomplished through the use of a lysis/binding buffer containing lithium chloride in high, preferably 10 molar concentration, which binds the RNA molecules to the carrier material used with a much higher affinity than it does the DNA molecules, the lysis and bonding of the ribonucleic acids to the silica carrier taking place in the same reaction vessel.

As already stated, a different binding specificity is achieved by the choice of lysis/binding buffer alone, so that the same carrier material can also be used for the isolation of RNA molecules. With that, it does not conform with the present theories concerning the physical and chemical mechanisms of binding nucleic acids to mineral materials under chaotropic conditions, according to which the adsorption of these nucleic acids on mineral matrixes takes place after the destruction of the hydrate sheaths of nucleic acids, brought about by the chaotropic salt. However, according to theoretical conjectures, this also means that single strands of DNA or RNA are bound so tightly to the mineral materials, that elution of the RNA can take place only at very high temperatures and, with that, also with damage to the RNA.

By using the carrier material described pursuant to the invention and by the use of lithium chloride for the lysis as well as for realizing the bonding of the RNA to the carrier material, the RNA can be eluted once again with DEPC-treated (diethyl pyrocarbonate-treated) water from the carrier without any problems.

A further decisive advantage of the inventive method, especially in connection with the isolation of long-chain genomic DNA and also of cellular total DNA, consists therein that the method requires no enzymatic pretreatment of the starting material whatsoever (proteinase treatments). Aside from its protein-denaturing effect (and, in this connection, also the inactivation of endogenous and exogenous DNAs and RNAs), the lysis buffer, used depending on the type of inactivation, also brings about the bonding of nucleic acids to the carrier material. This makes it possible, for example, to isolate genomic DNA from a monolayer cell culture, a tissue sample or from whole blood (for example, with $1 \times 10^5$ cells, 0.5 mg of tissue, 100 µL of whole blood), in fewer than 30 minutes. Lysis as well as bonding of the nucleic acids take place under the same buffering conditions and in the same reaction vessel. This also represents a decisive time advantage relative to other systems of isolating long-chain nucleic acids from such biological starting materials.

Aside from the isolation of the longer-chain DNA (genomic DNA) and RNA described, the carrier used is also suitable for the isolation and purification of nucleic acids from TAE gels and TBE gels, PCR fragments directly from the reaction mixtures (including the mineral oils present), as well as for the isolation of plasmid DNA from bacterial lysates. These possibilities are not dealt with further. Very high recovery rates of DNA fragments from gels or PCR mixtures ranging in size from 60 bp to 50 kbp and very high yields of qualitatively high-grade plasmid DNA are also realized here with the carrier material used.

The size of the nucleic acids, which are to be isolated or purified, preferably comprises the range from 50 to 60,000 nucleotides.

For all the applications described, the lysis buffer respectively used (consisting of guanidine thiocyanate, sodium iodide, guanidine hydrochloride or lithium chloride and appropriate detergent additions, depending on the application) also brings about the bonding of the nucleic acids to the carrier material. All nucleic acids from different starting materials, isolated with the inventive method and fixed to the carrier, are washed several times with a buffer (50 mM of NaCl; 10 mM of tris HCl, 1 mM of EDTA; 70 v/v [ethanol]). The buffer, used for the washing, differs from that in the original work described by Vogelstein and Gillepsie by a lower salt concentration and a higher ethanol concentration. Such a washing buffer composition permits more intensive washing without loss of bound nucleic acids. The elution of the nucleic acids is carried out, preferably, in an elution buffer (10 mM of tris HCl; 0.1 mM of EDTA) or in DEPC-treated water at a temperature of 48° to 56° C. and preferably of 52° C. within-a period of not more than 5 minutes.

Therefore the method according to the invention is also suitable for sensitive detection of apoptotic cells using the representation of nucleosomal DNA fragments. The specificity of the carrier material used, as described, allows the isolation of DNA fragments in a broad molecular spectrum (100 bp–>50 kbp) from cell lysates or tissue samples in which apoptosis is to be demonstrated. A typical characteristic of apoptosis is the presence of DNA ladders, which are formed by the presence of socalled nucleosomal DNA bands. According to the invention, even samples with fewer than $5 \times 10^4$ cells can be examined for the presence of such DNA ladders. Other isolation methods previously used for such detection require much larger amounts of cells. The method according to the invention requires less than 90 minutes, including electrophoresis separation of the DNA ladders. This makes it far superior to all methods previously used for the detection of apoptotic cells.

The isolated nucleic acids are available for a plurality of further molecular biological and biochemical methods, such as PCT/RT-PCR and special PR applications (LAXL-PCR, RAPD PCR fingerprinting, etc.), splitting with restriction endonucleases, clonings, sequencings, in vitro transcription, radioactive labeling, hybridization methods, etc.

The invention is described in the following by means of examples which, however, are not intended to limit the invention.

1. Isolation of Genomic DNA from a Eukaryontic Monolayer Cell Culture, Which was Cultivated on a 96—Well Microtiter Plate (approx. $5 \times 10^5$ Cells)

Remove the cell supernatant and rinse the cells twice briefly with 1×PBS.

Add 500 µL of lysis buffer (guanidine thiocyanate; N-lauryl sarcosyl; DTT; sodium citrate) directly to the well and transfer the cell suspension to a 1.5 mL Eppendorf centrifuge tube. Add 10 µL of the suspension produced from the carrier material used to the cell lysis suspension, swirl briefly, incubate for 5 minutes in an ice bath and subsequently pelletize the carrier material by centrifuging briefly in a table centrifuge (10 seconds). The genomic DNA, bound to the carrier pellet, is subsequently mixed with washing buffer (50 mM of NaCl; 10 mM of tris HCl; 1 mM of EDTA; 70% v/v ethanol) and washed 2 to 3 times. Subsequently, the genomic DNA is eluted from the carrier material at 52° C. by the addition of an elution buffer (10 mM of tris [HCl]; 0.1 mM of EDTA), the carrier is separated from the eluted, genomic DNA by centrifuging briefly and the latter is transferred to a new reaction vessel.

2. Isolation of Cellular Total RNA from a Hybridoma Cell Suspension (ca. 200 µL; ca. $10^3$ Cells)

Transfer the cell suspension to a 1.5 mL Eppendorf centrifuge tube and add 500 µL of lysis buffer (10M LiCl, 2% of Triton X-100). Incubate for 5 minutes at room temperature.

Add 10 µL of the suspension, produced from the carrier material used, to the cell lysis suspension, swirl briefly, incubate for 5 minutes in an ice bath and subsequently pelletize the carrier material by centrifuging briefly in a table centrifuge (10 seconds). The RNA, bound to the carrier pellet, is subsequently mixed with washing buffer (50 mM of NaCl; 10 mM of tris HCl; 1 mM of EDTA; 70% v/v) and washed 2 to 3 times. Subsequently, the cellular total RNA is eluted from the carrier material at 52° C. by the addition of DEPC-treated doubly distilled water, the carrier is separated from the eluted, cellular, total RNA by centrifuging briefly and transferred to a new reaction vessel.

3. Isolation of Genomic DNA from an Approximately 0.5 µL Trace of Blood on a Piece of Tissue Cut the region of tissue containing the trace of blood and transfer the cuttings to a 1.5 mL Eppendorf centrifuge tube. Add 500 µL of lysis buffer (guanidine thiocyanate; N-lauryl sarcosyl; sodium citrate) and incubate for some hours at room temperature.

Centrifuge briefly to separate the insoluble components, transfer the supernatant to a new centrifuge tube and add 10 μL of the suspension, produced from the carrier material used, swirl briefly, incubate for 5 minutes in an ice bath and subsequently pelletize the carrier material by centrifuging briefly in a table centrifuge (10 seconds). The genomic DNA, bound to the carrier pellet, is subsequently mixed once again with washing buffer (50 mM of NaCl; 10 mM of tris HCl; 1 mM of EDTA; 70% v/v ethanol) and washed 2 to 3 times. Subsequently, the genomic DNA is eluted from the carrier material at 52° C. by the addition of an elution buffer (10 mM tris [HCl]; 0.1 mM EDTA), the carrier is separated from the eluted, genomic DNA by centrifuging briefly and the latter is transferred to a new reaction vessel.

4. Isolation of Genomic DNA from Bone Material

Transfer approximately 100 to 250 mg of finely ground bone powder to a 2.0 mL Eppendorf centrifuge tube. Add 1 mL of lysis buffer (guanidine thiocyanate; N-lauryl sarcosyl; DTT; sodium citrate; 0.5M EDTA) and incubate at 56° C. with slight shaking for 15 to 20 hours.

Centrifuge at 12,000 to 14,000 rpm and transfer the supernatant to a new centrifuge tube.

Add 15 μL of the suspension, produced from the carrier material used, swirl briefly, incubate for 5 minutes in an ice bath and subsequently pelletize the carrier material by centrifuging briefly in a table centrifuge (10 seconds). The genomic DNA, bound to the carrier pellet, is subsequently mixed once again with washing buffer (50 mM of NaCl; 10 mM of tris HCl; 1 mM of EDTA; 70% v/v ethanol) and washed 3 times. Subsequently, the genomic DNA is eluted from the carrier material at 52° C. by the addition of an elution buffer (10 mM tris [HCl]; 0.1 mM EDTA), the carrier is separated from the eluted, genomic DNA by centrifuging briefly and the latter is transferred to a new reaction vessel.

5. Isolation of Genomic DNA from Stool Samples

Transfer about 100 mg of a stool sample to a 2.0 mL Eppendorf centrifuge tube and add 300 μL of a wash solution (sodium chloride, EDTA, tris HCl). Swirl for 30 seconds and subsequently centrifuge at 10,000 rpm for 2 minutes. Transfer the supernatant to a new 1.5 mL Eppendorf centrifuge tube and add 1 mL of lysis buffer (guanidine thiocyanate; N-lauryl sarcosyl; DTT; sodium citrate). Incubate at room temperature for 20 to 30 minutes.

Add 15 μL of the suspension, produced from the carrier material used, swirl briefly, incubate for 5 minutes in an ice bath and subsequently pelletize the carrier material by centrifuging briefly in a table centrifuge (10 seconds). The genomic DNA, bound to the carrier pellet, is subsequently mixed once again with washing buffer (50 mM of NaCl; 10 mM of tris HCl; 1 mM of EDTA; 70% v/v ethanol) and washed 3 times. Subsequently, the genomic DNA is eluted from the carrier material at 52° C. by the addition of an elution buffer (10 mM tris [HCl]; 0.1 mM EDTA), the carrier is separated from the eluted, genomic DNA by centrifuging briefly and the latter is transferred to a new reaction vessel.

6. Isolation of Genomic DNA from a Single Hair Root

Incubate a single hair root in volume of 500 μL of lysis buffer (guanidine thiocyanate; N-lauryl sarcosyl; DTT; sodium citrate) for 30 to 60 minutes at room temperature.

Add 15 μL of the suspension, produced from the carrier material used, swirl briefly, incubate for 5 minutes in an ice bath and subsequently pelletize the carrier material by centrifuging briefly in a table centrifuge (10 seconds). The genomic DNA, bound to the carrier pellet, is subsequently mixed once again with washing buffer (50 mM of NaCl; 10 mM of tris HCl; 1 mM of EDTA; 70% v/v [ethanol]) and washed 2 to 3 times. Subsequently, the genomic DNA is eluted from the carrier material at 52° C. by the addition of an elution buffer (10 mM tris [HCl]; 0.1 mM EDTA), the carrier is separated from the eluted, genomic DNA by centrifuging briefly and the latter is transferred to a new reaction vessel.

7. Purification of PCR Fragments Directly from the PCR Reaction Mixture

Add 150 μL of an immobilizing solution (6M sodium iodide with carrier suspension contained) directly to the PCR reaction mixture, including the overlaid layer of mineral oil. Swirl briefly and incubate for 3 minutes in an ice bath.

Pelletize the carrier material by centrifuging briefly in a table centrifuge (10 seconds). The PCR product, bound to the carrier pellet, is subsequently mixed once again with washing buffer (50 mM of NaCl; 10 mM of tris HCl; 1 mM of EDTA; 70% v/v ethanol) and washed twice. Subsequently, the PCR product is eluted from the carrier material at 52° C. by the addition of an elution buffer (10 mM of tris [HCl]; 0.1 mM of EDTA), the carrier is separated from the eluted PCR fragment by centrifuging briefly and the latter is transferred to a new reaction vessel.

8. Detection of Apoptosis in a Monolayer Cell Culture ($1 \times 10^5$ cells)

Direct lysis of the cells in a 1.5 or 2.0 mL Eppendorf reaction vessel, with addition of 1 mL lysis buffer (guanidine thiocyanate; N-lauryl sarcosyl; DTT; sodium citrate). Incubation for 5 minutes at room temperature.

Addition of 20 mL of the suspension produced from the carrier material used, brief vortexing and incubation for 5 minutes. Pelleting of the carrier material by means of a brief centrifugation step and disposal of the top fraction. Washing of the DNA fragments bound to the carrier pellet with a washing buffer (50 mM NaCl; 10 mM tris; 1 mM EDTA; 70% ethanol) and again brief centrifugation (10 s; 10,000 rpm). Complete removal of the washing buffer and final elution of the DNA fragments bound on the carrier material by means of an elution buffer (1 mM EDTA; 10 mM tris) at 52° C. and separation of the top fraction containing the nucleic acids from the carrier material by means of brief centrifugation.

Analysis of the isolated nucleic acid on a 1.5% agarose gel to characterize the apoptotic nucleosomal DNA bands.

9. Differential Isolation of Cytoplasmatic Nucleosomal DNA Bands and Intact Core DNA from a Monolayer Cell Culture of $1 \times 10^5$ cells Pelleting of the cells after cell harvesting. Addition of 400 μL of a hypotonic lysis buffer 15 mM tris; 15 mM EDTA; 0.52% Triton X-100) and incubation for 15 minutes on ice. Centrifugation at 14,000 rpm for 15 minutes to separate the cytoplasmatic fraction from intact chromatin.

A. Isolation of Apoptotic DNA Fragments from the Cytoplasmatic Top Fraction

Transfer of the top fraction to a new reaction vessel and addition of 1 mL of a binding buffer (6 M sodium iodide)

and of 20 µL of the suspension produced from the carrier material used. Incubation for 5 minutes and subsequent pelleting of the carrier material.

Washing of the DNA fragments bound to the carrier pellet with a washing buffer (50 mM NaCl; 10 mM tris; 1 mM EDTA; 70%/o ethanol) and again brief centrifugation (10 s; 10,000 rpm). Complete removal of the washing buffer and final elution of the DNA fragments bound on the carrier material by means of an elution buffer (1 mM EDTA; 10 mM tris) at 52° C. and separation of the top fraction containing the DNA fragments from the carrier material by means of brief centrifugation.

B. Isolation of the Intact Core DNA from the Chromatin Pellet

Lysis of the pellets with addition of 1 mL lysis buffer (guanidine thiocyanate; N-lauryl sarcosyl; DTT; sodium citrate). Incubation for 5 minutes at room temperature. Addition of 20 µL of the suspension produced from the carrier material used, brief vortexing and incubation for 5 minutes. Pelleting of the carrier material by means of a brief centrifugation step and disposal of the top fraction. Washing of the nucleic acids bound to the carrier pellet with a washing buffer (50 mM NaCl; 10 mM tris; 1 mM EDTA; 70% ethanol) and again brief centrifugation (10 s; 10,000 rpm). Complete removal of the washing buffer and final elution of the nucleic acids bound on the carrier material by means of an elution buffer (1 mM EDTA; 10 mM tris) at 52° C. and separation of the top fraction containing the nucleic acids from the carrier material by means of brief centrifugation.

Analysis of the isolated nucleic acid on a 1.5% agarose gel to characterize the apoptotic nucleosomal DNA bands from the cytoplasmatic fraction and the intact core DNA (highly chromosomal DNA).

We claim:

1. A universal process for isolating and purifying nucleic acids from extremely small amounts of highly contaminated biological starting materials by
   a) lysis of the biological starting materials containing nucleic acids, with buffers containing at least one chaotropic salt of high ionic strength,
   b) incubation with a highly disperse, non-porous, unstructured and homogeneous silica carrier, the silica particles having a particle size of 7 to 40 nm and an active surface area of 50 to 300 $m^2/g$,
   c) separation of the nucleic acids fixed to the carrier, from the lysate,
   d) washing the nucleic acids fixed to the surface of the carrier, with a washing buffer and
   e) eluting the nucleic acids from the carrier with a buffer of low salt concentration,
   wherein the biological starting materials are chosen from the group consisting of less and 0.5 mg of tissue material, less than 0.5 µL blood or blood traces on clothing, less than 5 µL of saliva, and fewer than $10^3$ cells of different biological starting materials.

2. The method of claim 1, wherein the chaotropic salt is chosen from the group consisting of guanidine hydrochloride, guanidine thiocyanate, lithium chloride, sodium iodide, potassium iodide, sodium perchlorate and lithium chloride/urea mixtures with ionic strengths in excess of 4M.

3. The method of claim 1, wherein the silica carrier is highly dispersed, non-porous, unstructured and homogeneous, chemically pure silica, with a particle size of 40 nm and a specific surface area of 50 $m^2/g$.

4. The method of claim 1, wherein the lysis of the starting material containing the nucleic acids, and the bonding of the nucleic acids to the carrier particles, are carried out in the same reaction vessel.

5. The method of claim 1, wherein the carrier with the bound nucleic acids is separated from the remaining lysate by a brief centrifuging step.

6. The method of claim 1, wherein the nucleic acids, fixed to the carrier, are washed with a washing buffer consisting of 50 mM of sodium chloride, 10 mM of tris hydrochloride, 1 mM of EDTA, and 70% ethanol.

7. The method of claim 1, wherein the nucleic acids fixed to the carrier, are eluted with a buffer of low ionic strength, comprising 10 mM of tris hydrochloride, 0.1 mM of EDTA, other low salt buffers or DEPC treated at a temperature of 48° to 56° C.

8. The method of claim 1, wherein it is carried out as a batch method.

9. The method of claim 1, wherein it is used for the rapid isolation of genomic desoxyribonucleic acid and cellular total ribonucleic acid.

10. The method of claim 1, wherein it is used for the isolation and purification of PCR products or PCR fragments and for the isolation of DNA fragments from aqueous solutions and TAE or TBE agarose gels in a broad molecular spectrum.

11. The method of claim 1, wherein, for the isolation of ribonucleic acids, the lysis of the biological starting material is carried out with 10 molar lithium chloride and the lysis and binding of the ribonucleic acids on the silica carrier are carried out in the same reaction vessel.

12. The method of claim 1, wherein the size of the nucleic acids, which are to be isolated or purified, comprises the range from 50 nucleotides to 60,000 nucleotides.

13. The method according to claim 1, wherein it is used for the detection of apoptotic cells using ladders.

* * * * *